(12) United States Patent
Ferrell et al.

(10) Patent No.: US 9,662,412 B2
(45) Date of Patent: May 30, 2017

(54) PLASMA VAPOR CHAMBER AND ANTIMICROBIAL APPLICATIONS THEREOF

(71) Applicant: EP Technologies LLC, Akron, OH (US)

(72) Inventors: James Ferrell, Stow, OH (US); Erinn R. Bogovich, Ravenna, OH (US); Robert L. Gray, Kent, OH (US); Daphne Pappas Antonakas, Hudson, OH (US); Tsung-Chan Tsai, Cuyahoga Falls, OH (US); Sameer Kalghatgi, Copley, OH (US)

(73) Assignee: EP Technologies LLC, Akron, OH (US)

( * ) Notice: Subject to any disclaimer, the term of this patent is extended or adjusted under 35 U.S.C. 154(b) by 0 days.

(21) Appl. No.: 15/041,102

(22) Filed: Feb. 11, 2016

(65) Prior Publication Data

US 2016/0228592 A1  Aug. 11, 2016

Related U.S. Application Data

(60) Provisional application No. 62/114,899, filed on Feb. 11, 2015.

(51) Int. Cl.
*A61L 2/20* (2006.01)
*H05H 1/24* (2006.01)
*A61L 2/14* (2006.01)

(52) U.S. Cl.
CPC ............ *A61L 2/14* (2013.01); *H05H 1/2406* (2013.01); *A61L 2202/122* (2013.01); *H05H 2001/2412* (2013.01)

(58) Field of Classification Search
USPC .......... 250/538, 526; 422/1, 4, 5, 11, 24, 26, 422/22, 28, 29, 40, 120, 121, 186,
(Continued)

(56) References Cited

U.S. PATENT DOCUMENTS 5,872,359 A * 2/1999 Stewart .................. A61L 2/208
250/339.09
5,920,799 A 7/1999 Graves
(Continued)

FOREIGN PATENT DOCUMENTS

EP         1356828 A1    10/2003
WO    2014145570 A1     8/2014

OTHER PUBLICATIONS

Klämpfl, T.G., et al., Cold atmospheric air plasma sterilization against spores and other microorganisms of clinical Interest. Applied and Environmental Microbiology, 2012. 78(15): p. 5077-5082.

(Continued)

*Primary Examiner* — Bernard Souw
(74) *Attorney, Agent, or Firm* — Calfee, Halter & Griswold LLP (57) ABSTRACT

Exemplary apparatuses and methods of killing or deactivating bacteria are disclosed herein. An exemplary apparatus for killing or deactivating bacteria includes a plasma vapor chamber. The plasma vapor chamber has a vapor inlet for allowing a vapor into the chamber, a high voltage electrode, one or more grounding electrodes. The one or more grounding electrodes at least partially surrounding the plasma vapor chamber. The plasma vapor chamber includes an outlet for allowing fluid to flow out of the chamber. When the chamber is filled with vapor for a period of time sufficient to saturate the chamber with vapor, the high voltage electrode is energized to generate plasma throughout the chamber.

20 Claims, 7 Drawing Sheets

(58) Field of Classification Search
USPC ......... 422/186.04; 134/30, 56 R, 57 R, 95.3, 134/102.1, 102.2, 200, 201; 204/164, 204/526, 527
See application file for complete search history.

(56) References Cited

U.S. PATENT DOCUMENTS

| | | | | |
|---|---|---|---|---|
| 6,706,243 | B1 * | 3/2004 | Sias | A61L 2/14 134/102.2 |
| 6,875,399 | B2 * | 4/2005 | McVey | A61L 2/208 250/339.13 |
| 6,969,487 | B1 * | 11/2005 | Sias | A61L 2/14 422/1 |
| 7,008,592 | B2 * | 3/2006 | Sias | A61L 2/14 422/1 |
| 2003/0132100 | A1 | 7/2003 | Crowe et al. | |
| 2015/0038584 | A1 * | 2/2015 | Fridman | A01N 37/46 514/562 |
| 2015/0306258 | A1 * | 10/2015 | Ferrell | A01N 1/0215 422/28 |

OTHER PUBLICATIONS

Machala, Z., et al., Formation of ROS and RNS in Water Electro-Sprayed through Transient Spark Discharge in Air and their Bactericidal Effects. Plasma Processes and Polymers, 2013. 10(7): p. 649-659.
Park, D.P., et al., Reactive nitrogen species produced in water by non-equilibrium plasma increase plant growth rate and nutritional yield. Current Applied Physics, 2013. 13: p. S19-S29.
Oehmigen, K., et al., The role of acidification for antimicrobial activity of atmospheric pressure plasma in liquids. Plasma Processes and Polymers, 2010. 7(3-4): p. 250-257.
Pappas, D., Status and potential of atmospheric plasma processing of materials. Journal of Vacuum Science & Technology A, 2011. 29(2): p. 020801.
Gaunt, L.F., C.B. Beggs, and G.E. Georghiou, Bactericidal action of the reactive species produced by gas-discharge nonthermal plasma at atmospheric pressure: a review. Plasma Science, IEEE Transactions on, 2006. 34(4): p. 1257-1269.
Hayashi, N., et al., Sterilization of medical equipment using radicals produced by oxygen/water vapor RF plasma. Japanese journal of applied physics, 2006. 45(10S): p. 8358.
Cabiscol, E., J. Tamarit, and J. Ros, Oxidative stress in bacteria and protein damage by reactive oxygen species. International Microbiology, 2010. 3(1): p. 3-8.
Laroussi, M. and F. Leipold, Evaluation of the roles of reactive species, heat, and UV radiation in the inactivation of bacterial cells by air plasmas at atmospheric pressure. International Journal of Mass Spectrometry, 2004. 233(1): p. 81-86.
Lukes, P., et al., Aqueous-phase chemistry and bactericidal effects from an air discharge plasma in contact with water: evidence for the formation of peroxynitrite through a pseudo-second-order post-discharge reaction of $H2O2$ and $HNO2$. Plasma Sources Science and Technology, 2014. 23(1): p. 015019.
von Woedtke, T., et al., Plasma-liquid interactions: chemistry and antimicrobial effects, in Plasma for Bio-Decontamination, Medicine and Food Security. 2012, Springer. p. 67-78.
Bruggeman, P. and C. Leys, Non-thermal plasmas in and in contact with liquids. Journal of Physics D: Applied Physics, 2009. 42(5): p. 053001.
Joshi, S.G., et al., Nonthermal dielectric-barrier discharge plasma-induced inactivation involves oxidative DNA damage and membrane lipid peroxidation in *Escherichia coli*. Antimicrobial agents and chemotherapy, 2011. 55(3): p. 1053-1062.
Matthes, R., et al., Antimicrobial Efficacy of Two Surface Barrier Discharges with Air Plasma against In Vitro Biofilms. PloS one, 2013. 8(7): p. e70462.
Andrade, F.J., et al., A new, versatile, direct-current helium atmospheric-pressure glow discharge. Journal of Analytical Atomic Spectrometry, 2006. 21(11): p. 1175-1184.
Zhu, W. and J.L. Lopez, A dc non-thermal atmospheric-pressure plasma microjet. Plasma Sources Science and Technology, 2012. 21(3): p. 034018.
Blajan, M., et al., Emission spectroscopy of pulsed powered microplasma for surface treatment of PEN film. Industry Applications, IEEE Transactions on, 2011. 47(3): p. 1100-1108.
Lerouge, S., M. Wertheimer, and Y. L'H, Plasma sterilization: a review of parameters, mechanisms, and limitations. Plasmas and Polymers, 2001. 6(3): p. 175-188.
Misra, N., et al., Nonthermal plasma inactivation of food-borne pathogens. Food Engineering Reviews, 2011. 3(3-4): p. 159-170.
Sosnin, E.A., et al., The effects of UV irradiation and gas plasma treatment on living mammalian cells and bacteria: a comparative approach. Plasma Science, IEEE Transactions on, 2004. 32(4): p. 1544-1550.
Daifas, D.P., et al., Effect of ethanol vapor on growth and toxin production by Clostridium botulinum in a high moisture bakery product. Journal of food safety, 2000. 20(2): p. 111-125.
Gil, M.I., et al., Fresh-cut product sanitation and wash water disinfection: problems and solutions. International journal of food microbiology, 2009. 134(1): p. 37-45.
Niemira, B.A., Cold Plasma Decontamination of Foods. Annual Review of Food Science and Technology, 2012. 3: p. 125-142.
Pankaj, S.K., et al., Applications of cold plasma technology in food packaging. Trends in Food Science & Technology, 2014. 35(1): p. 5-17.
Sosnin, Edward A. et al., "The Effects of UV Irradiation and Gas Plasma Treatment on Living Mammalian Cells and Bacteria: A comparative Approach," IEEE Transactions on Plasma Science, vol. 32, No. 4, Aug. 2004; pp. 1544-1550.
Pankaj, S.K., et al., "Applications of cold plasma technology in food packaging," Trends in Food Science & Technology, 35 (2014) pp. 5-17.
Gil, Maria I., et al., "Fresch-cut product sanitation and wash water disinfection: Problems and solutions," International Journal of Food Microbiology, 134 (2009); pp. 37-45.
Daifas, Daphne Phillips, et al., "Effect of ethanol vapor on growth and toxin production of clostridium botulinum in a high moisture bakery product," Journal of Food Safety 20 (2000); pp. 111-125.
Niemira, Brendan A, "Cold Plasma Decontamination of Foods," Annual Review of Food Science and Technology; Mar. 2012; pp. 125-142.f.
Lerouge, S., et al., Plasma Sterilization: A review of parameters, Mechanisms, and Limitations; Plasmas and Polymers, vol. 6. No. 3, Sep. 2001; pp. 175-188.

* cited by examiner

PLASMA VAPOR CHAMBER AND ANTIMICROBIAL APPLICATIONS THEREOF

RELATED APPLICATIONS

This non-provisional utility patent application is based on and claims priority to U.S. Provisional Patent Application Ser. No. 62/114,899 titled, PLASMA VAPOR CHAMBER AND ANTIMICROBIAL APPLICATIONS THEREOF, which was filed on Feb. 11, 2015, and which is incorporated herein by reference in its entirety.

TECHNICAL FIELD

The present invention relates generally to plasma vapor chambers and more particularly to applications thereof.

BACKGROUND

Several literature reports have provided scientific evidence of the antimicrobial activity of cold plasmas operating under atmospheric pressure conditions. The antimicrobial properties of the aforementioned plasmas have been attributed to the presence of ultraviolet radiation, reactive oxygen (ROS), and nitrogen (RNS) species. It is believed that the chemical content of plasmas simulates the natural defense system of multi-cellular organisms that use physiological processes that employ ROS in order to kill foreign microorganisms. The primary biological targets for ROS include DNA, proteins and lipids. The plasma-induced mechanisms currently proposed to interpret bacterial death include, i) electrostatic disruption of cell membranes and ii) membrane or cytoplasmic oxidation, both of which lead to lipid damage, irreversible conformations in the membrane structure, pore formation, and membrane catastrophe. Plasma-generated species may include: superoxides ($O_2^-$), hydroxyl radicals ($OH^-$), ozone ($O_3$), hydrogen peroxide ($H_2O_2$), nitric oxide (NO), nitrites ($NO_2$), nitrates ($NO_3$) and peroxynitrite ($ONOO^-$). Some of the above mentioned molecules and chemical moieties are found in commercially available liquid disinfectant solutions. Some highly potent radicals (e.g. peroxynitrite), however, are short-lived and therefore would most likely need to be applied immediately after they are produced to ensure rapid disinfection. A strength of plasma usage for decontamination efforts is the mixture of dynamic, antimicrobial ROS and RNS because collectively these species place substantial stress on microbial physiology.

Microorganisms possess enzymatic countermeasures to deal with stressors in their local environments, including superoxide dismutase, catalase, peroxidase, etc., but after a critical plasma application threshold, these enzymes cannot clear the oxidative stress, and the microbes ultimately succumb to the applied plasma exposure. The combination of rapid, potent antimicrobial radicals with more stable species that still possess antimicrobial efficacy (nitrates) makes it very difficult for microbes to develop resistance to a synergistic plasma effect.

Application of atmospheric cold plasmas upon pathogenic bacteria such as E. coli and S. aureus suspended in water or other liquid biological media has been successfully demonstrated. However, the application of atmospheric plasmas in complex, real life settings, such as nosocomial environments, would require direct contact of the plasma with dry contaminated surfaces.

Sterilization of medical equipment using radicals produced by oxygen/water vapor RF plasma has been reported, but the proposed process involved the use of vacuum equipment rendering it inapplicable for large area disinfection. The most distinctive chemical feature of the cold plasma processes presented in this paper is their ability to cause multiple chemical reactions at atmospheric pressure and room temperature. Another paper presented a 1.5 $\log_{10}$ ($CFU/cm^2$) reduction for S. epidermidis and 1.8-2.0 $\log_{10}$ ($CFU/cm^2$) for P. aeruginosa residing on polycarbonate discs after 30 s-600 s of treatment with air surface barrier discharge.

SUMMARY

Exemplary apparatuses and methods of killing or deactivating bacteria are disclosed herein. An exemplary apparatus for killing or deactivating bacteria includes a plasma vapor chamber. The plasma vapor chamber has a vapor inlet for allowing a vapor into the chamber, a high voltage electrode, one or more grounding electrodes. The one or more grounding electrodes at least partially surrounding the plasma vapor chamber. The plasma vapor chamber includes an outlet for allowing fluid to flow out of the chamber. When the chamber is filled with vapor for a period of time sufficient to saturate the chamber with vapor, the high voltage electrode is energized to generate plasma throughout the chamber.

Another exemplary apparatus for killing or deactivating bacteria includes a plasma vapor chamber, a vapor inlet for allowing a vapor into the chamber, a high voltage electrode, one or more grounding electrodes and an outlet for allowing fluid to flow out of the chamber. When the chamber is filled with vapor for a period of time sufficient to saturate the chamber with vapor; the high voltage electrode is energized to generate plasma in the vapor.

An exemplary methodology of killing or deactivating bacteria includes introducing a vapor to a chamber for a first period of time and generating plasma in the chamber for a second period of time to create reactive species, that is for about 1 minute or less and contacting a surface containing bacteria with the reactive species.

DETAILED DESCRIPTION

In exemplary embodiments of the inventions herein, the antimicrobial activity of air and mixtures of non-thermal (cold) plasmas using air with vaporized water and ethanol are demonstrated. Without limiting effect, it is believed that the use of vaporized liquids within a confined plasma reactor system result in potent antimicrobial species that can be used in surface disinfection applications. In some embodiments described herein the surfaces are non-tissue or organ surface. In some embodiments, the surface may be a tissue or organ. In some embodiments, the use of ethanol vapor as an initial gaseous media source may serve as an additional source of antimicrobial species generated in the plasma vapor chamber. In some embodiments, the use of vaporized liquids in order to create plasma may result in potent antimicrobial processes within a reaction system and allow for decontamination of recalcitrant microorganisms or difficult to sanitize substrates.

FIG. 1 is an exemplary embodiment of a plasma vapor chamber 100. Plasma vapor chamber 100 includes a high voltage electrode 112 made out of a conductive material, such as, for example copper. In this exemplary embodiment, the high voltage copper electrode had an outer dimension of 38.1 mm and an inner dimension of 25.4 mm. Plasma vapor chamber includes a ground electrode 109. The high voltage electrode 112 and ground electrode 109 were configured and designed to generate a dielectric barrier discharge (DBD) plasma. In this exemplary embodiment, an acrylic housing 101 was used. The acrylic housing 101 had the following dimensions: height, 100 mm; inner diameter, 41.28 mm, and outer diameter; 50.80 mm.

High voltage electrode 101 was connected to a high voltage wire 113 that went through cap 102 located on the top of the plasma vapor chamber 100. High voltage electrode 101 may have any suitable shape to create plasma inside the plasma vapor chamber 100. Ground electrode 109 may take any suitable shape to create the desired plasma. In some embodiments, ground electrode 109 may be a mesh. In some embodiments, ground electrode 109 may be a mesh that surrounds or partially surrounds plasma vapor chamber 100. In some embodiments, multiple ground electrodes 109 may be used.

In some embodiments, the plasma 150 is created throughout the plasma vapor chamber 100. In some embodiments, the plasma 150 is created in one or more locations within the plasma vapor chamber 100. In some embodiments, the plasma 150 is created throughout the plasma vapor chamber 100 however it is concentrated in one or more locations. In some embodiments, the plasma 150 is created in more than about 10% of the volume of the plasma vapor chamber 100. In some embodiments, the plasma 150 is created in more than about 20% of the volume of the plasma vapor chamber 100. In some embodiments, the plasma 150 is created in more than about 30% of the volume of the plasma vapor chamber 100. In some embodiments, the plasma 150 is created in more than about 40% of the volume of the plasma vapor chamber 100. In some embodiments, the plasma 150 is created in more than about 60% of the volume of the plasma vapor chamber 100. In some embodiments, the plasma 150 is created in more than about 10% of the volume of the plasma vapor chamber 100. Cap 102 was a polypropylene cap. A rubber gasket 111 was located between cap 102 and housing 101. A dielectric barrier 114 was located on the bottom of the high voltage electrode 112 with the remaining surfaces surrounded by a non-conductive housing 116, which in this case was Ultem™ polyetherimide resin (SABIC America, Houston, Tex.). The dielectric barrier 114 was quartz and had a thickness of 1 mm.

The high voltage electrode 112 was connected to a microsecond pulsed power supply (not shown) manufactured by Advanced Plasma Solutions, Malvern Pa. The operating voltage and frequency were 20 kV and 3.5 kHz respectively. The pulse duration was set at 10 μs. The base 103 of the vapor chamber 100 was made of a Teflon® supported ground conductor 109 which was made of stainless steel electrode. The gap between the electrode 112 and the ground electrode 109 was kept maintained at 2 mm. The vapor chamber 101 was also equipped with two gas inlets 106 and two gas outlet ports 108 that allowed the introduction and exhaust of gases into the vapor chamber 100. Although particular materials, sizes and configurations are disclosed in this one embodiment, different materials, sizes, and power settings may be used. In addition, other plasma sources may be utilized in some embodiments.

The following parameters and set-up (not shown) were used to generate vapor. Bench-mounted nitrogen and oxygen gas cylinders were connected to single valve gas flow controllers with high pressure tubing. Additional lines were utilized to provide gases to an air free glass bubbler. Five mL of prepared ethanol/water solutions at concentrations varying from pure water to pure ethanol were introduced into the bubbler. Mixtures of nitrogen with oxygen at various ratios were used to vaporize the liquid in the bubbler. An additional line was then connected from the bubbler to an inlet 106 connected to the vapor chamber 100 to allow the transport of the vaporized liquids along with their carrier gases.

In the exemplary embodiments, cold plasma was generated using the following settings: 3.5 KHz, 20 kV, 10 μs pulse duration, and a 100% duty cycle. The total flow rate of the gases introduced into the chamber ranged from 100-500 standard cubic centimeters per minute (sccm), but was fixed at one specific flow rate for the duration of plasma generation. The average power transferred to the discharge ranged from 1.5 to 3.1 W. The power measurements were taken from an energy monitor (Watts Up™ 57777 Energy Monitor, Think Tank Energy Products, Inc., Milton, Vt.).

Substrates 152 were loaded, with the bacteria inoculated surface 153 facing the high voltage electrode 112, into the vapor chamber 101 and were set on the grounded electrode 109 and the vapor chamber 100 was sealed. The vaporized liquids were introduced into the vapor chamber and allowed to saturate the vapor chamber for 1 minute prior to plasma generation for each sample. The mist was exposed to plasma for periods of time from 5 seconds to 1 minute. Following treatment in the plasma vapor chamber 100, the exposed substrates were placed into centrifuge tubes that contained sterile de-ionized water for bacterial evaluation.

The following bacteria strands and media were used. *E. coli* ATCC 35150 (Type Culture Collection, Manassas, Va.) was used in the experiments described herein. All prepared cultures were grown overnight to reach logarithmic growth phase within brain heart infusion broth (BHIB; Difco, Becton Dickinson, Franklin Lakes, N.J.), composed of 6.0 g/L brain heart infusion (from solids), 6.0 g/L peptic digest of animal tissue, 5.0 g/L sodium chloride, 3.0 g/L dextrose, 14.5 g/L pancreatic digest of gelatin, and 2.5 g/L disodium phosphate at a final pH of 7.4.

The Initial overnight bacterial cultures had an approximate concentration of $1.0 \times 10^9$ CFU (colony formation units)/mL. Ten μL of the bacterial suspension (in nutrient-rich BHIB) was aseptically pipetted onto the surface of sterile stainless steel disks (1 cm diameter; Muzeen & Blythe, Montreal) or freshly obtained, washed baby spinach leaves (1 cm×1 cm cut squares). The substrates were air dried in a Thermo Scientific 1300 Series biosafety cabinet (Pittsburgh, Pa.) for 90 minutes.

Surviving bacteria was detected using the following procedures. Bacterial viability was assessed immediately after plasma exposure. Sample tubes containing plasma-exposed substrates were serially diluted in order to obtain dilutions of experimental samples and then applied to brain heart infusion agar (BHIA) plates. Liquid aliquots (0.1 mL) for each sample at each dilution factor were pipetted aseptically on the surface of BHIA plates. This method is known as the spread plate method and is commonly used for antimicrobial assessment. Results are expressed through the $\log_{10}$ reduction (LR) term which corresponds to:

$$LR = \log_{10}\left(\frac{A}{B}\right)$$

Where A and B represent the number of viable bacterial colonies that are present before and after plasma treatment, respectively. The pour plate method was also performed in order to assess larger amounts of overall bacterial inoculum at a given time. Briefly, BHIA was prepared and slowly cooled to 45° C. The entire sample (at a given dilution factor) was poured into an empty, sterile, plastic Petri dish (100×15 mm). A 15 mL aliquot of the cooled agar was mixed slowly to the sample and gently swirled for 30 seconds. The plates were left undisturbed until the agar solidified. For both methods, the inoculated plates were incubated at 37° C. for 18 hours. Bacterial cell enumeration were collected the following day with the Neutec Flash and Grow Colony Counter, (Neutec, Farmingdale, N.Y.). Data was analyzed with GraphPad Prism and InStat graphical and statistical software (GraphPad Software, Inc., La Jolla, Calif.).

A USB4000-UV-VIS (Ocean Optics, Dunedin, Fla.) spectrometer with a DET4-200-850 detector and order-sorting filter to cover the (200-850 nm) wavelength range was employed in order to analyze emission spectra generated with different nitrogen:oxygen gas mixtures and ethanol vapor concentrations. The spectrometer had an optical resolution of 1.5 nm and was equipped with a multi-band pass order-sorting filter and a 25 μm entrance slit. An optical fiber was fixed in place 5 mm beyond one of the gas outlet ports and connected back to the spectrometer. Spectra were taken from a discharge gap 2 mm from the discharge to the substrate. Measurements were obtained over the duration of 30 seconds of plasma exposure. OES spectra were collected by accompanied Ocean Optics software and analyzed using Spectrum Analyzer open freeware (version 1.7).

Experimental Results

A. Role of Gas Mixtures i) Air Plasmas of Various $N_2/O_2$ Concentrations.

Figure 1:
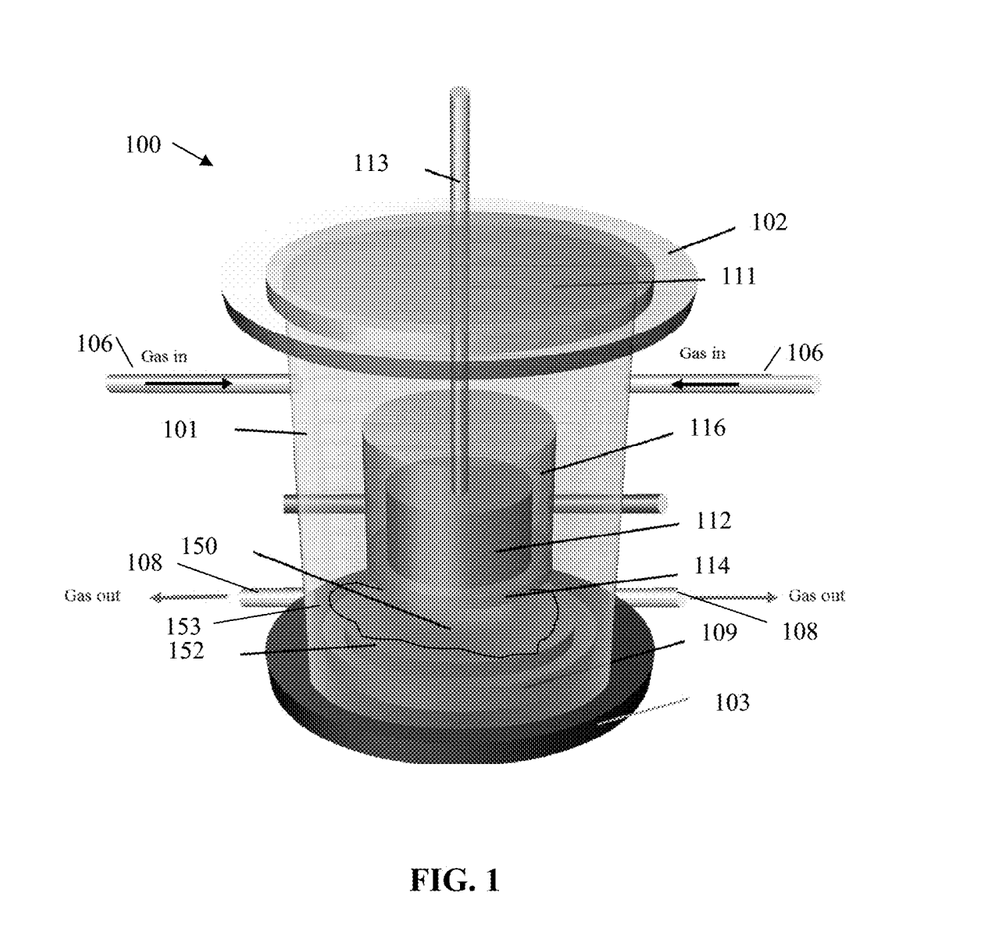
FIG. 1 is an exemplary embodiment of a plasma vapor chamber.
Figure 2:
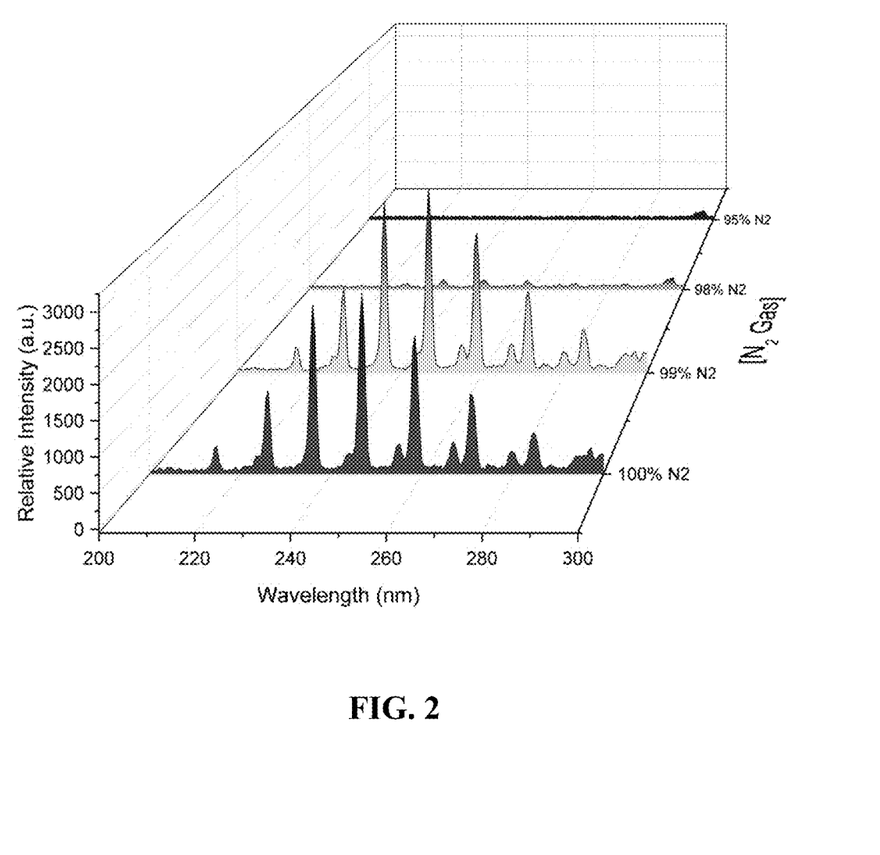
FIG. 2 is a graph showing spectral lines of several different nitrogen to oxygen gas ratios using optical emission spectroscopy.
Figure 3:
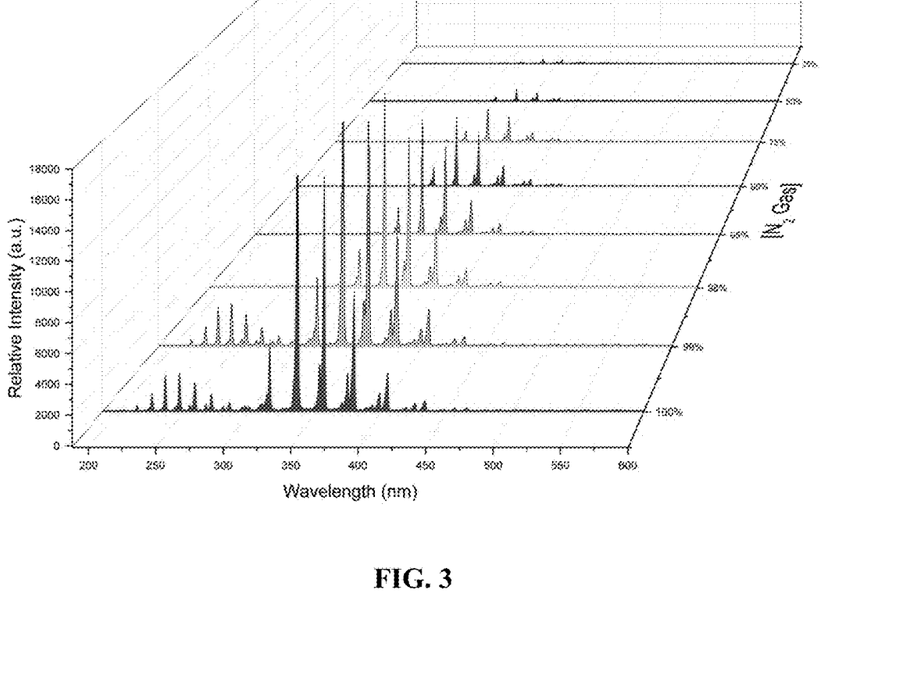
FIG. 3 is another three-dimensional graph showing spectral lines of several nitrogen to oxygen gas ratios using optical emission spectroscopy.
Figure 4:
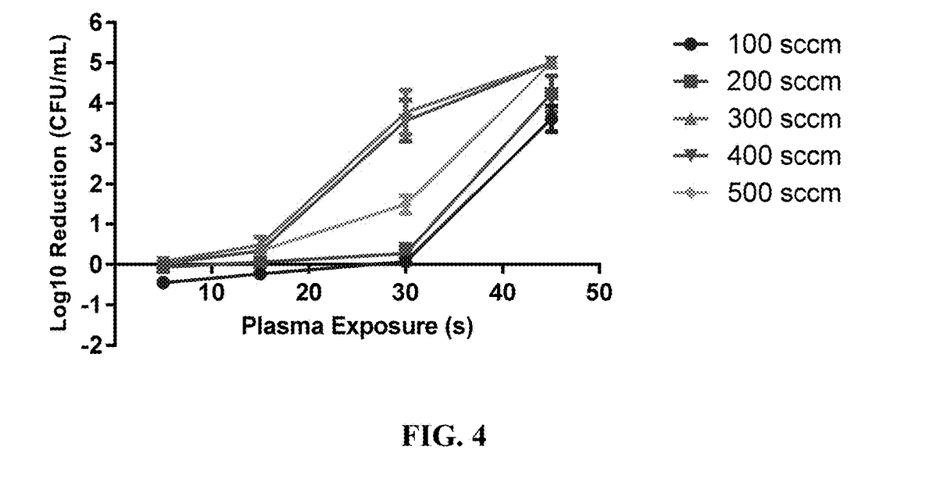
FIG. 4 is a graphical representation of E. coli ATCC 35150 viability log reduction after treatment in the plasma vapor chamber for different total flow rates of gas mixtures and water vapor.
Figure 5:
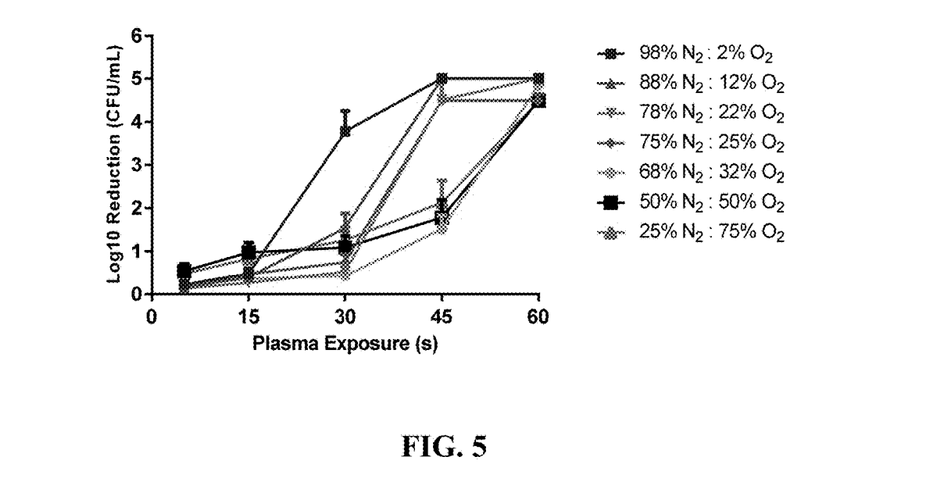
FIG. 5 is a graphical representation E. coli ATCC 35150 viability log reduction after treatment in the plasma vapor chamber using differing nitrogen to oxygen gas ratios and water vapor.
Figure 6:
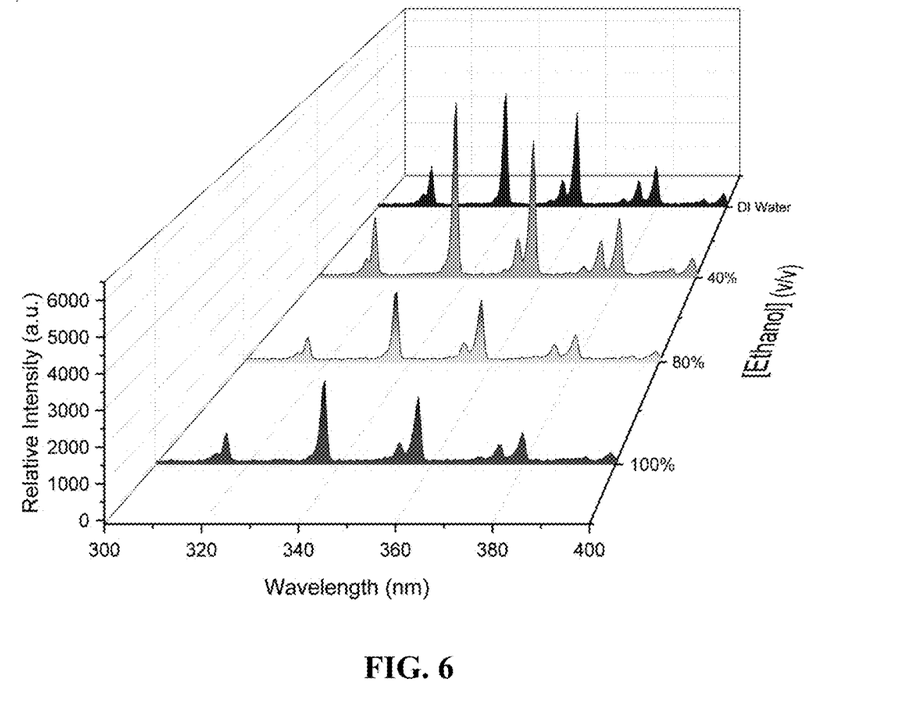
FIG. 6 is another three-dimensional graph showing spectral lines of ethanol vapor-mediated plasma delivered by nitrogen and oxygen using optical emission spectroscopy.

Optical emission spectroscopy was employed to analyze the plasma phase and to obtain information on the presence of active species that have the potential to contribute to the antimicrobial activity of the plasma. Optical emission spectra collected in the UV-Vis-NIR region (200-600) are illustrated in FIGS. 2 and 3. The molecular nitrogen emission bands dominate the obtained spectra in gas mixtures composed of high nitrogen concentration. The spectra were collected from discharges using the following gas mixtures: 98% $N_2$:2% $O_2$, 75% $N_2$:25% $O_2$, 50% $N_2$:50% $O_2$, and 25% $N_2$:75% $O_2$. These spectra were collected from the plasma vapor chamber 100 via a port located near the bottom of the chamber. The above mentioned spectra were collected without ethanol vapor being present in the discharge.

The captured spectra (200-300) in the ultraviolet range seen in FIG. 2 present a series of unique peaks that can be attributed to the presence of NO. The illustrated spectrum was observed in the discharge generated from gas mixtures that contained four different ratios of nitrogen and oxygen. There are a series of intense bands that range from (230-270) nm, particularly with 99% $N_2$:1% $O_2$ gas mixtures. These intense bands can be assigned to the NOγ (A-X) system. It is believed that the generation of the NO species is an indication of extensive $O_2$ and $N_2$ dissociation at temperatures higher that 1600 K or due to direct electron impact. The role of $N_2$ metastables and their collisions form NO based on the following reactions are known:

$$N_2(A)+NO(X) \rightarrow N_2(X)+NO(A) \tag{1}$$

$$NO(A) \rightarrow NO(X)+h\nu(NO\gamma) \tag{2}$$

The role of NO is critical, as its emissivity in the UV-C range of the electromagnetic spectrum contributes to the disruption of viral and bacterial membranes. UV-C light can directly attack cellular DNA leading to cell death while it inhibits their ability to spread.

Increase of the oxygen content in mixtures presented in FIG. 2, demonstrated quenching of the NO bands. The appearance of fewer and weaker NO peaks in the (180-280) nm range indicate that the gas temperatures increased with increasing amount of $O_2$. This is due to the fact that oxygen as an electronegative gas tends to consume free electrons towards the formation of $O^-$ and $O_2^-$ anions. Therefore, higher energy is required to sustain the discharge when the oxygen concentration is increased and results in overall higher gas temperature. However, an increase in temperature is not responsible for the antimicrobial efficacy observed in the experimental results. Measurements of experimental substrates immediately after exposure indicated the samples remained at room temperature.

FIG. 3 illustrates another portion of the collected UV-Vis spectrum, ranging from 200-300). The intensity of the 337.1 nm peak for various $O_2$—$N_2$ concentrations represents the (0-0) C-B transition of $N_2$ in the second positive system. An increase of the oxygen concentration leads to a dramatic decrease of the intensity of this spectral line.

ii) Air Plasmas Containing Ethanol Vapor.

In additional experiments, ethanol-water mixtures were vaporized and carried by a gas mixture containing 78% nitrogen and 22% oxygen, designed to mimic the concentrations found in room air. The concentration of ethanol vapor in the bubbler for this portion of the study was 80% (v/v %) in $H_2O$. The limit of detection for antimicrobial efficacy was 5.0 logs (99.999% reduction). Some of the objectives of these experiments were to determine optimal flow rates of gas used to carry vaporized liquid to the reaction chamber that promote antimicrobial efficacy.

The experimental results demonstrated very limited antimicrobial efficacy with 5 seconds of plasma exposure across all flow rates studied. At 15 seconds of exposure, a differential trend between the flow rates was observed. There was a −0.232 log reduction (LR), 0.059 LR, 0.484 LR, 0.339 LR, and 0.346 LR for flow rates of 100, 200, 300, 400, and 500 sccm respectively. Thirty seconds of plasma exposure provided results that displayed significant difference between the total gas flow rate into the plasma vapor chamber. Log reductions of 0.067 and 0.273 were associated with total flow rates of 100 and 200 sccm. When the flow rate increased to 300 sccm, a 3.78 LR was observed. At 400 and 500 sccm, LR values of 3.569 and 1.491 were observed. At 45 seconds, there is significant antimicrobial efficacy across all of the flow rates studied. Log reductions of 3.615 and 4.234 were observed at 100 and 200 sccm. Higher flow rates all displayed complete kill that reached the limit of detection.

FIG. 4 illustrates the average values for all log reductions across all flow rates. The antimicrobial efficacy was best when the flow rate was at 300 sccm for the combined gas mixture. However, 400 sccm also had similar log reduction values. As the flow rate of the gas mixture increased to 500 sccm, the efficacy dropped at lower plasma exposure durations. In this exemplary embodiment, the optimal gas flow rate appears to be between (300-400) sccm for this chamber configuration. It is believed that the residence time of the plasma-derived species also plays a role in this observation. It is believed that a certain flow rate needs to be applied in order to create a sufficient concentration of actives. In some embodiments, bacterial kill may be promoted through the mechanical dislodging of the bacteria from contaminated surfaces.

The total flow rate of the combined nitrogen and oxygen gases was set at 300 sccm for the below experimentation with respect to plasma exposure times and various $N_2$ to $O_2$ ratios. The concentration of ethanol vapor in the bubbler for these experiments was set at 80%. The limit of detection for antimicrobial efficacy on stainless steel coupons was 5.0 logs (99.999% reduction). As shown in FIG. 5, the percentage of nitrogen in oxygen was varied from 98% to 25%. High nitrogen content within the plasma (98%) displayed the following log reduction ("LR") values: 0.221 with 5 seconds of plasma exposure, 0.484 with 15 seconds of plasma exposure, 3.776 with 30 seconds of plasma exposure, 5 with 45 seconds of plasma exposure, and 5 with 60 seconds of plasma exposure. Plasmas generated with nitrogen at overall percentages of 88% and 78% displayed excellent germicidal efficacy against *E. coli*, particularly after 45 seconds and 60 seconds of exposure. Generally, log reduction values for 30 seconds and below were fairly poor with plasmas composed of less than 78% nitrogen. However, there was a spike in antimicrobial efficacy for plasma exposure intervals 30 seconds and below for plasma discharges composed of 50% oxygen and 75% oxygen.

The effect of vapor from various ethanol concentrations in water was also investigated. Ethanol vapor was generated with the use of a bubbler system as described previously. The concentration of ethanol vapor and its effect on antimicrobial efficacy of bacteria introduced into the plasma vapor chamber is discussed below. Optical emission spectra data was also collected for ethanol vapor and is shown in FIG. 6. Initial ethanol concentrations supplied to the bubbler was varied from 0% (deionized water) to 100% (pure ethanol). The total flow rate of combined nitrogen and oxygen was set at 300 sccm. The composition of the combined gas mixture was 78% nitrogen and 22% oxygen. The spectrum collected from plasmas generated with 80% ethanol displayed emission bands between (245-250) nm and 681 nm where increased nitric oxide peaks were present. The proportion of the nitrogen lines found in the (300-400) nm (FIG. 6) was highest in the de-ionized water spectrum. The molar concentration of ethanol, water, and nitrogen: oxygen gas vapor delivered to the plasma vapor chamber was determined for each spectral characterization. For the 80% ethanol solution, 2.923% ethanol, 2.374% water, and 94.703% nitrogen:oxygen gas was delivered to the chamber. For the 40% ethanol solution, 1.261% ethanol, 6.147% water, and 92.592% nitrogen:oxygen gas.

To study the effect of vaporized ethanol plasmas on *E. coli,* 3 plasma exposure durations were selected: 15 seconds, 30 seconds, and 45 seconds. Results from the microbial testing show that the 15 second exposure displayed relatively low antimicrobial efficacy across all ethanol vapor concentrations. Thirty seconds of plasma exposure resulted in LR values >2 (99%) with 80% and 90% ethanol concentrations. Forty-five seconds of plasma exposure resulted in LR values >3 (99.9%) with 40% and 60% ethanol concentrations. Log reductions increased even further to the limit of detection, 5 logs (99.999%), with 70% and 80% ethanol concentrations. The log reduction values dropped from 5 to 2.716 when the concentration of the ethanol delivered inside the plasma vapor chamber increased from 80% to 90%. Furthermore, the use of 100% ethanol resulted in very poor antimicrobial efficacy and marked a strong transition point away from previous ethanol concentration log reduction values (FIG. 7).

The experiments determined that there is an optimal ethanol range that can be used in vaporized form. The reduction in antimicrobial efficacy at high ethanol vapor concentrations likely stems from oversaturation of the plasma vapor chamber with ethanol. Elevated concentration of ethanol and its oxidized forms (e.g. acetaldehyde and acetic acid) may prevent formation of minimum threshold concentrations of ROS or RNS due to oversaturation.

B. Application of Air Plasmas Containing Ethanol Vapor on Spinach Leaves and Stainless Steel The effect of the experimental substrate was also investigated. The results presented above were collected from stainless steel coupons only. The total flow rate of combined nitrogen and oxygen (at a gas composition mixture of 78% and 22% respectively) was fixed at 300 sccm. This mixture of gas was chosen in order to mimic ambient air and represent plasmas that could be generated in a more cost effective manner. The use of room air instead of defined gas canisters expands applications into more practical settings. Three plasma discharge exposure durations were selected: 15 seconds, 30 seconds, and 45 seconds.

FIG. 8A compares log reduction differences between substrates based on ethanol concentration and the substrate type: stainless steel (SS) or spinach leaves (SP). A biological substrate (spinach) was chosen to evaluate possible differences between abiotic and biotic substrate effects on plasma antimicrobial efficacy. Log reduction values for spinach leaves are nearly half of those for stainless steel coupons across all plasma exposure groups for low concentrations of ethanol vapor (40%). This observed trend continues, but is not as pronounced by the maximum plasma exposure time point of 45 seconds for substrates exposed to 60% ethanol vapor. Log reduction differences between the substrates continued to be present with 80% ethanol vapor, but log reduction values of 1.799 and 3.765 were observed on spinach leaves after 30 and 45 seconds of exposure respectively. These values were ~1.5 logs less than their counterparts on stainless steel coupons.

The log reduction between the stainless steel and spinach can be attributed to spinach leaves being a more complex substrate. These complex substrates are rough and uneven when compared to smooth, stainless steel coupons. Machined substrates are relatively consistent whereas biological samples are unique, even sample to sample. The challenge for using plasmas on biological samples or tissues is the topography of the sample, its localized environment (soil load, liquid vs. dry, etc.), and response to the plasma. Biological samples such as leaves may also outgas in physiological response to plasmas, further affecting localized species activity generated from plasmas in the vicinity of the treated surface.

Figure 8A:
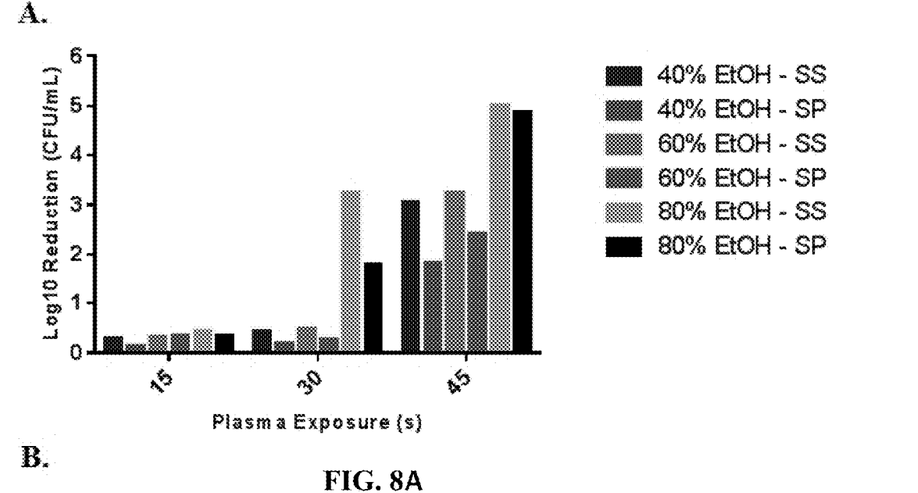
FIGS. 8A and 8B are graphical representations of *E. coli* ATCC 35150 viability log reduction in plasma reactor comparing abiotic (stainless steel coupons) versus biotic (baby spinach leaves) surfaces using nitrogen and oxygen to deliver vapor to the plasma vapor chamber, with different ethanol concentrations and different overall total gas flow rate.
Figure 8B:
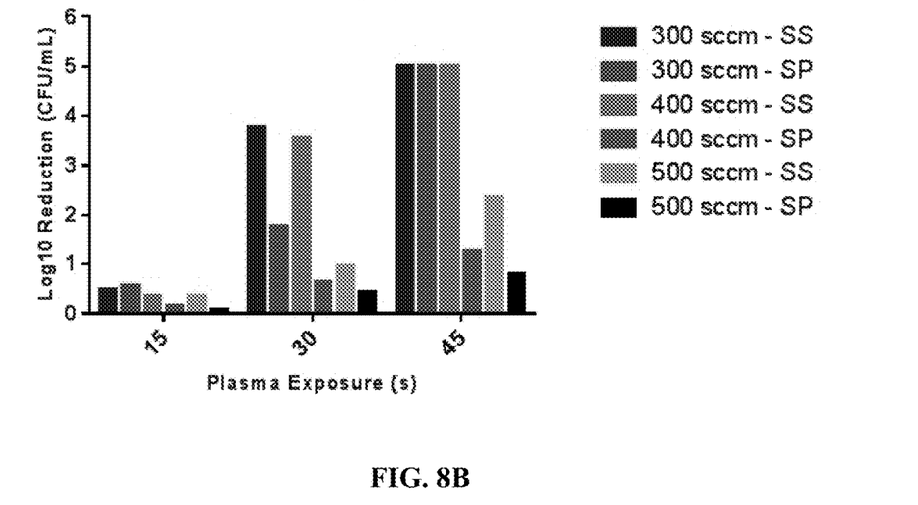

FIG. 8B illustrates differences between biotic and abiotic surfaces and possible effects on antimicrobial effects generated by the plasma vapor system described previously. The gas composition mixture of nitrogen and oxygen was set at 78% and 22% respectively. An 80% ethanol solution was provided for the vapor study. Three plasma discharge exposure durations were selected: 15 seconds, 30 seconds, and 45 seconds. A flow rate of 300 sccm did not significantly differ between stainless steel coupons and spinach leaves. The LR values remained fairly consistent between the two substrates. However, when the flow rate was adjusted to 400 and 500 sccm, LR values for the stainless steel coupons were markedly different from those generated from spinach leaves.

Figure 9:
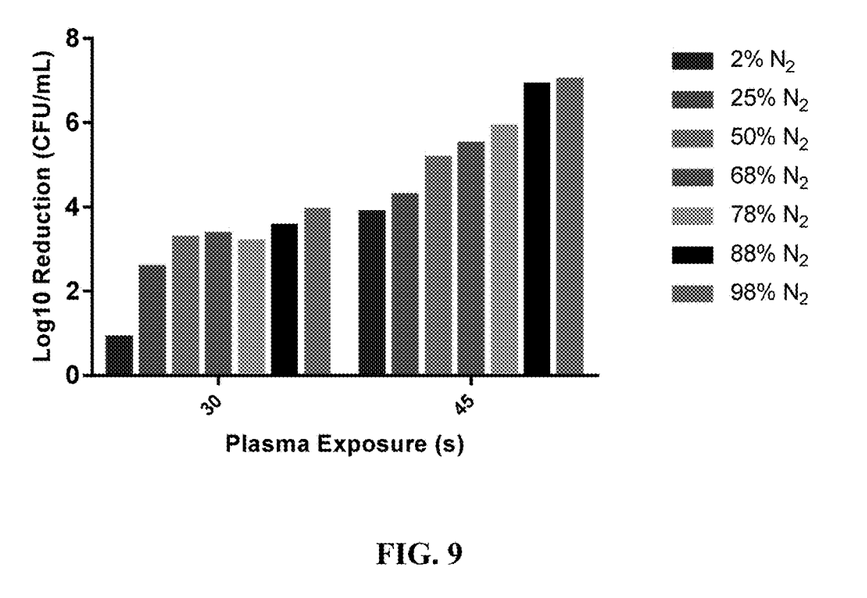
FIG. 9 is a graphical representation *E. coli* ATCC 35150 viability log reduction in after treatment in the plasma vapor chamber using different nitrogen to oxygen gas mixtures and water vapor; pour plate method used to assess heightened antimicrobial efficacy.

Antimicrobial efficacy was investigated further with the use of the pour plate method described previously. This method was used to evaluate a higher total volume of bacterial culture and increase the limit of detection for the purpose of antimicrobial calculations and subsequently confirm previous results. In the earlier experiments, the maximum limit of detection was 5.0 logs, a maximum that correlated to a 99.999% reduction in bacterial viability. This method increased the limit of detection by 2 additional logs, correlating to an assay of 100× more sensitivity. A maximum measurement with this assay, correlated to a 99.99999% reduction in bacterial viability. A range of nitrogen:oxygen gas flow ratios were used to transport 80% ethanol vapor downstream into the plasma reactor chamber for plasma exposure durations of 30 and 45 seconds respectively. In both exposure groups, a consistent trend was observed. As shown in FIG. 9, thirty seconds of plasma exposure resulted in LR values >2 logs (99%) across all nitrogen:oxygen mixtures and reached nearly 4 logs with high nitrogen content (98%). Forty-five seconds resulted in LR values >4 logs (99.99%) across all nitrogen:oxygen mixtures are reached nearly 7 logs (99.99999%), the limit of detection for this study, with high nitrogen content (98%).

Experimental results indicate that there are optimal ranges for different experimental variables during the application of plasma vapor within a chamber electrode configuration. For example, the total flow rate of the combined gaseous medium should be optimized during plasma application. In these experiments, a total gas flow rate of (300-400) sccm resulted in the most substantial antimicrobial efficacy. The flow rate and subsequently the plasma residence time of the reactive species also likely play a role in this observation. It was discovered that the composition of the initial feed gas medium contributed significantly to the overall antimicrobial efficacy. The combination of mixtures found to be most antimicrobial were those with high nitrogen. While, low nitrogen and high oxygen did ultimately provide multi-log antimicrobial efficacy, it did so only after 60 seconds of continuous exposure. High nitrogen discharges achieved LR values of 4+ (99.99% kill) within half of that the time as low nitrogen discharges. It is believed that the high nitrogen compositions likely produce nitric oxide, which is a known powerful antimicrobial species. Optical emission spectroscopy identified intense peaks between (220-270) nm that can be assigned to nitric oxide, these peaks diminish significantly as the concentration of fed nitrogen within the initial gas medium into the reactor chamber drops below 98%.

Figure 7:
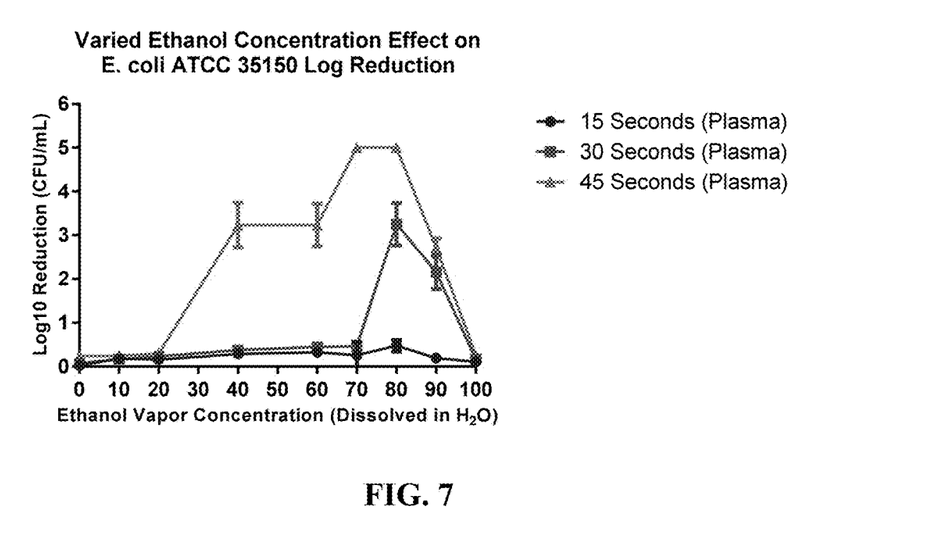
FIG. 7 is a graphical representation E. coli ATCC 35150 viability log reduction after treatment in the plasma vapor chamber using ethanol vapor concentration delivered by nitrogen and oxygen.

Ethanol vapor delivered into the chamber also was found to have an optimal concentration gradient. FIG. 7 illustrates that ethanol concentrations as low as 40% can be used to generate multi-log reductions in pathogenic bacteria after 45 seconds of plasma exposure on stainless steel coupons within the plasma vapor chamber. The optimal ethanol concentration range was determined to be between about 70 to about 80%. This concentration range showed highly significant antimicrobial efficacy after 45 seconds of continuous plasma exposure. Furthermore, this ethanol concentration range also resulted in multi-log antimicrobial efficacy after just 30 seconds of plasma exposure.

FIG. 8A illustrates that the ethanol concentration variable results in values that differ by 1-2 logs between stainless steel coupons and spinach leaves. The antimicrobial efficacy based on the total flow rate of the gas does not seem to differ significantly between substrates for rates less than 400 sccm. Once the flow rate increases, dramatic differences between the efficacies of the two substrates as shown in FIG. 8B.

We claim:

1. An apparatus for killing or deactivating bacteria comprising:
   a chamber;
   a vapor inlet for allowing a vapor into the chamber;
   a high voltage electrode;
   one or more grounding electrodes, at least partially surrounding the chamber;
   an outlet for allowing fluid to flow out of the chamber;
   wherein the chamber is filled with vapor for a period of time sufficient to saturate the chamber with vapor; and
   the high voltage electrode is energized to generate plasma throughout the chamber.

2. The apparatus of claim 1 wherein the plasma is focused in one or more locations in the chamber.

3. The apparatus of claim 1 wherein the one or more grounding electrodes are placed in locations around the chamber, and wherein the placement of the one or more grounding electrodes cause the plasma to be focused in one or more locations in the chamber.

4. The apparatus of claim 1 wherein one or more of the grounding electrodes are formed with mesh.

5. The apparatus of claim 1 wherein the vapor replaces substantially all of the ambient air in the chamber.

6. The apparatus of claim 1 further comprising a bubbler in fluid communication with the vapor inlet.

7. The apparatus of claim 6 further comprising a source of nitrogen to flow through the bubbler.

8. The apparatus of claim 7 further comprising a source of oxygen to flow through the bubbler.

9. The apparatus of claim 8 wherein the flow rate of nitrogen and oxygen is between about 200 and 500 sccm.

10. The apparatus of claim 8 wherein the flow rate of nitrogen and oxygen is between about 300 and 400 sccm.

11. An apparatus for killing or deactivating bacteria comprising:
    a chamber;
    a vapor inlet for allowing a vapor into the chamber;
    a high voltage electrode;
    one or more grounding electrodes;
    an outlet for allowing fluid to flow out of the chamber;

wherein the chamber is filled with vapor for a period of time sufficient to saturate the chamber with vapor; and
the high voltage electrode is energized to generate plasma in the vapor.

12. The apparatus of claim 11 further comprising a vapor.

13. The apparatus of claim 12 vapor comprises a mixture of nitrogen and oxygen.

14. The apparatus of claim 13 wherein the ratio of nitrogen to oxygen is greater than 1 to 1.

15. The apparatus of claim 13 wherein the ratio of nitrogen to oxygen is greater than 40 to 1.

16. The apparatus of claim 13 wherein the nitrogen comprises greater than about 98% of the one or more gases.

17. The apparatus of claim 12 wherein the vapor comprises a mixture of vaporized alcohol and water.

18. The apparatus of claim 17 wherein the alcohol is ethanol.

19. The apparatus of claim 18 wherein the vapor comprises less than 90% ethanol (v/v %) in water.

20. The apparatus of claim 18 wherein the vapor comprises between 40% and 90% ethanol (v/v %) in water.

* * * * *